United States Patent
Ferro et al.

(10) Patent No.: US 11,622,813 B2
(45) Date of Patent: *Apr. 11, 2023

(54) INTRAOPERATIVE SYSTEMS AND METHODS FOR DETERMINING AND PROVIDING FOR DISPLAY A VIRTUAL IMAGE OVERLAID ONTO A VISUAL IMAGE OF A BONE

(71) Applicant: AOD Holdings, LLC, Arroyo Grande, CA (US)

(72) Inventors: Thomas D. Ferro, Arroyo Grande, CA (US); Scott Gill, Arroyo Grande, CA (US); Austin Ferro, Arroyo Grande, CA (US); Donald Lee, Arroyo Grande, CA (US); Joe Phillips, Arroyo Grande, CA (US)

(73) Assignee: AOD HOLDINGS, LLC, Arroyo Grande, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/864,576

(22) Filed: Jul. 14, 2022

(65) Prior Publication Data

US 2022/0346880 A1 Nov. 3, 2022

Related U.S. Application Data

(63) Continuation of application No. 16/567,975, filed on Sep. 11, 2019, now abandoned, which is a (Continued)

(51) Int. Cl.
*A61B 5/00* (2006.01)
*A61B 5/11* (2006.01)
(Continued)

(52) U.S. Cl.
CPC ............ *A61B 34/10* (2016.02); *A61B 5/0077* (2013.01); *A61B 5/064* (2013.01); *A61B 5/1079* (2013.01);
(Continued)

(58) Field of Classification Search
None
See application file for complete search history.

(56) References Cited

U.S. PATENT DOCUMENTS

| 6,348,058 B1 | 2/2002 | Melkent et al. |
| 8,021,162 B2 | 9/2011 | Sui |

(Continued)

FOREIGN PATENT DOCUMENTS

WO   WO 2015/089118   6/2015

OTHER PUBLICATIONS

Li et al., "Augmented Virtuality for Arthroscopic Knee Surgery", Medical Image Computing and Computer Assisted Intervention (MICCAI), pp. 185-192, 2011.

*Primary Examiner* — David H Chu
(74) *Attorney, Agent, or Firm* — McDonnell Boehnen Hulbert & Berghoff LLP

(57) ABSTRACT

Example methods and systems may be used intraoperatively to help surgeons perform accurate and replicable surgeries, such as knee arthroplasty surgeries. An example system combines real time measurement and tracking components with functionality to compile data collected by the hardware to register a bone of a patient, calculate an axis (e.g., mechanical axis) of the leg of the patient, assist a surgeon in placing cut guides, and verify a placement of an inserted prosthesis.

20 Claims, 13 Drawing Sheets

Related U.S. Application Data continuation of application No. 16/260,251, filed on Jan. 29, 2019, now Pat. No. 10,449,004, which is a continuation of application No. 16/106,404, filed on Aug. 21, 2018, now Pat. No. 10,231,786, which is a continuation of application No. 15/261,356, filed on Sep. 9, 2016, now Pat. No. 10,092,361.

(60) Provisional application No. 62/217,185, filed on Sep. 11, 2015.

(51) Int. Cl.

| | | |
|---|---|---|
| *A61B 34/20* | (2016.01) | |
| *A61B 34/10* | (2016.01) | |
| *A61B 90/00* | (2016.01) | |
| *A61B 5/107* | (2006.01) | |
| *G06T 19/00* | (2011.01) | |
| *G16H 50/50* | (2018.01) | |
| *A61B 5/06* | (2006.01) | |
| *A61B 34/00* | (2016.01) | |

(52) U.S. Cl.
CPC .......... *A61B 5/1127* (2013.01); *A61B 5/4504* (2013.01); *A61B 5/4887* (2013.01); *A61B 5/7425* (2013.01); *A61B 34/20* (2016.02); *A61B 90/361* (2016.02); *G06T 19/006* (2013.01); *G16H 50/50* (2018.01); *A61B 5/11* (2013.01); *A61B 5/743* (2013.01); *A61B 2034/105* (2016.02); *A61B 2034/107* (2016.02); *A61B 2034/108* (2016.02); *A61B 2034/2055* (2016.02); *A61B 2034/2065* (2016.02); *A61B 2034/252* (2016.02); *A61B 2090/3983* (2016.02); *A61B 2505/05* (2013.01); *A61B 2576/00* (2013.01); *G06T 2210/41* (2013.01)

(56) References Cited

U.S. PATENT DOCUMENTS

| | | |
|---|---|---|
| 8,165,659 B2 | 4/2012 | Sheffer et al. |
| 8,876,830 B2 | 11/2014 | Hodorek et al. |
| 9,508,106 B1 | 11/2016 | Salmassy |
| 10,092,361 B2 | 10/2018 | Ferro et al. |
| 10,231,786 B2 | 3/2019 | Ferro et al. |
| 10,449,004 B2 | 10/2019 | Ferro et al. |
| 10,467,752 B2 | 11/2019 | Tanji |
| 10,743,939 B1 | 8/2020 | Lang |
| 2005/0215879 A1 | 9/2005 | Chuanggui |
| 2005/0256389 A1 | 11/2005 | Koga et al. |
| 2006/0029917 A1 | 2/2006 | Sui |
| 2006/0281971 A1 | 12/2006 | Sauer et al. |
| 2007/0179626 A1 | 8/2007 | de la Barrera et al. |
| 2008/0195109 A1 | 8/2008 | Hunter et al. |
| 2008/0319491 A1 | 12/2008 | Schoenefeld |
| 2009/0043556 A1 | 2/2009 | Axelson et al. |
| 2010/0030232 A1 | 2/2010 | Zehavi et al. |
| 2010/0292703 A1 | 11/2010 | Couture |
| 2011/0275957 A1 | 11/2011 | Bhandari |
| 2012/0294498 A1 | 11/2012 | Popovic |
| 2013/0261433 A1 | 10/2013 | Daon |
| 2014/0163568 A1 | 6/2014 | Wong et al. |
| 2014/0330279 A1 | 11/2014 | Park et al. |
| 2014/0378978 A1 | 12/2014 | Park |
| 2015/0070347 A1 | 3/2015 | Hofmann et al. |
| 2015/0245878 A1 | 9/2015 | Jaramaz et al. |
| 2015/0305817 A1 | 10/2015 | Kostrewski |
| 2016/0302871 A1 | 10/2016 | Gregerson et al. |
| 2017/0148180 A1 | 5/2017 | Elenbaas et al. |
| 2020/0000523 A1 | 1/2020 | Ferro et al. |

INTRAOPERATIVE SYSTEMS AND METHODS FOR DETERMINING AND PROVIDING FOR DISPLAY A VIRTUAL IMAGE OVERLAID ONTO A VISUAL IMAGE OF A BONE

CROSS REFERENCE TO RELATED APPLICATION

The present disclosure is a continuation of and claims priority to U.S. patent application Ser. No. 16/567,975, filed on Sep. 11, 2019, which is a continuation of and claims priority to U.S. patent application Ser. No. 16/260,251, filed on Jan. 29, 2019, which is a continuation of and claims priority to U.S. patent application Ser. No. 16/106,404, filed on Aug. 21, 2018, which is a continuation of and claims priority to U.S. patent application Ser. No. 15/261,356, filed on Sep. 9, 2016, which claims priority to U.S. patent application No. 62/217,185, filed on Sep. 11, 2015, the entire contents of each of which are herein incorporated by reference.

FIELD

The present disclosure relates generally to collecting information of a bone of a limb of a patient and providing for display a virtual image overlaid onto a visual model of the bone, and more particularly to recognizing a position and a movement of the bone in physical space and recognizing a position and a movement of a surgical device in physical space so as to provide information for assistance of placement of the surgical device at a position on the bone based on the position and the movement of the surgical device in physical space.

BACKGROUND

During orthopedic knee arthroplasties, the worn out bone and cartilage are removed and replaced with various biocompatible implants to take the place of the resected bone and cartilage. Knee arthroplasty usually includes a femoral component that is fixed onto a distal end of a femur, and tibial components that include a tibial tray and an intermediate component. To affix these components to the bone, a series of cuts are made to the distal end of the femur and a proximal end of the tibia. To make these cuts in the bones, surgeons use a variety of cut guides that are used to guide a blade of a bone saw through the bones of the patient.

Many modern orthopedic knee arthroplasties use computer assistance to help the surgeon perform an accurate and replicable surgery. Currently, "navigation" systems are used for the computer to register the bone. These systems are able to help verify and estimate a general surface of the bone through a probing sequence that is timely and cumbersome for surgeons. After the bone is registered, it is required during knee arthroplasties that mechanical axes of the leg are discovered to be able to make the distal cut to the femur perpendicular to the axes. Many systems use an intramedullary rod and/or an extramedullary rod, while others use contact infrared probes.

Therefore, there is a need for a system that is able to accurately register the bone in real time, calculate the mechanical axes of the leg without probes, and be able to guide the surgeon to accurately place the implant/prosthesis through a real time measurement array.

SUMMARY

In one example, a system is described that includes a measurement device to collect information of a surface of a bone of a limb of a patient, to track one or more reference points positioned on one or more bones or an anatomy of the patient, and to track one or more reference points positioned on a surgical device. The system also includes one or more processors, and data storage including instructions executable by the one or more processors for performing functions. The functions comprise determining a visual model of the bone based on the collected information of the surface of the bone, recognizing a position and a movement of the bone in physical space based on the tracked reference points positioned on the one or more of the bone or the anatomy of the patient and causing the visual model of the bone to reflect the position and the movement of the bone in physical space, recognizing a position and a movement of the surgical device in physical space based on the tracked reference points positioned on the surgical device, and providing for display a virtual image overlaid onto the visual model of the bone, wherein the virtual image includes information for assisting in placement of the surgical device at a position on the bone based on the position and the movement of the surgical device in physical space.

In another example, a method is described comprising receiving information, collected by a measurement device, of a surface of a bone of a limb of a patient, determining a visual model of the bone based on the collected information of the surface of the bone, recognizing a position and a movement of the bone in physical space based on tracked reference points positioned on the one or more of the bone or the anatomy of the patient and causing the visual model of the bone to reflect the position and the movement of the bone in physical space, recognizing a position and a movement of a surgical device in physical space based on tracked reference points positioned on the surgical device, and providing for display a virtual image overlaid onto the visual model of the bone, wherein the virtual image includes information for assisting in placement of the surgical device at a position on the bone based on the position and the movement of the surgical device in physical space.

In another example, a non-transitory computer-readable medium is described having stored thereon instructions that when executed by a computing device that includes one or more processors causes the computing device to perform functions. The functions comprise receiving information, collected by a measurement device, of a surface of a bone of a limb of a patient, determining a visual model of the bone based on the collected information of the surface of the bone, recognizing a position and a movement of the bone in physical space based on tracked reference points positioned on the one or more of the bone or the anatomy of the patient and causing the visual model of the bone to reflect the position and the movement of the bone in physical space, recognizing a position and a movement of a surgical device in physical space based on tracked reference points positioned on the surgical device, and providing for display a virtual image overlaid onto the visual model of the bone, wherein the virtual image includes information for assisting in placement of the surgical device at a position on the bone based on the position and the movement of the surgical device in physical space.

The features, functions, and advantages that have been discussed can be achieved independently in various embodiments or may be combined in yet other embodiments further details of which can be seen with reference to the following description and drawings.

BRIEF DESCRIPTION OF THE FIGURES

The novel features believed characteristic of the illustrative embodiments are set forth in the appended claims. The illustrative embodiments, however, as well as a preferred mode of use, further objectives and descriptions thereof, will best be understood by reference to the following detailed description of an illustrative embodiment of the present disclosure when read in conjunction with the accompanying drawings, wherein:

DETAILED DESCRIPTION

Disclosed embodiments will now be described more fully hereinafter with reference to the accompanying drawings, in which some, but not all of the disclosed embodiments are shown. Indeed, several different embodiments may be described and should not be construed as limited to the embodiments set forth herein. Rather, these embodiments are described so that this disclosure will be thorough and complete and will fully convey the scope of the disclosure to those skilled in the art.

Example methods and systems described below may help surgeons make cuts to the bone during surgeries, such as knee arthroplasty replacement surgeries. An example system can be used intraoperatively to register a surface of the bone to be cut in real time with a measurement device. The system will then track, with spatial awareness, the bone to calculate mechanical axes of the leg. The system then assists the surgeon in placing the cut guides in a correct position onto the bone. To do this, the system uses an array of measuring devices to provide real time data as well as object tracking when the surgeon moves the cut guides. In further examples, the system uses augmented reality with the real time measurement array to assist the surgeon with placement of the cut guides by displaying virtual cutting planes onto a live image of the bone produced in reference to the physical cut guide before the cut guide is fixed into place.

Example modes of implementation are described below as one of many ways that the embodiments may be carried out. The systems may include hardware and software computing components to enable a surgical procedure, along with physical components needed to guide the surgeon during the procedure.

Figure 1:
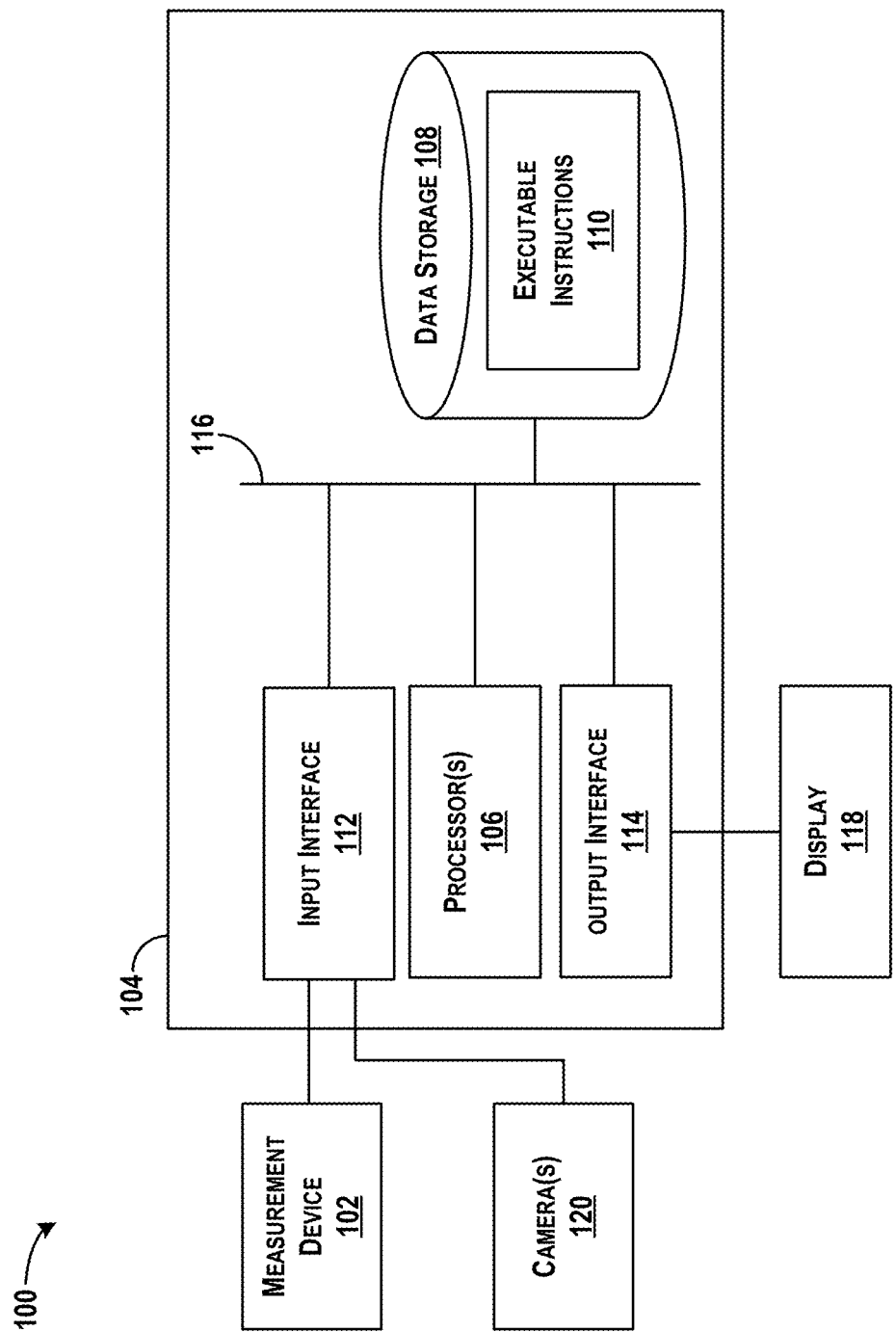
FIG. 1 is a block diagram of a system, according to an example embodiment.

Referring now to FIG. 1, a block diagram of a system 100 is illustrated, according to an example embodiment. The system 100 includes a measurement device(s) 102, a computing device 104, a display 118, and camera(s) 120.

The measurement device(s) 102 may collect information of a surface of a bone of a limb of a patient, track one or more reference points positioned on one or more bones or an anatomy of the patient, and track one or more reference points positioned on a surgical device. The measurement device(s) 102 thus is used to register the bone, as well as track movement of the bone and of surgical devices. As one example, the measurement device(s) 102 may track different features of the anatomy of the patient as well as virtual reference points to aid in determining mechanical axes of the leg, and track and measure spatially surgical devices such as cut guides, and also measure spatially a final placement of the prosthesis.

The measurement device(s) 102 may be, but is not limited to, any non-contact active measurement device, non-contact passive measurement device, or non-contact three-dimensional (3D) scanning device. In other examples, the measurement device(s) 102 may include a high acquisition rate laser scanner, a scanner attached to an articulating arm, or a corded mobile scanner. The measurement device(s) 102 may be operated using technologies such as time-of-flight, triangulation, conoscopic holography, structured light, modulated light, laser, infrared, stereoscopic 3D imaging, or any combination of the aforementioned technologies. One or more of these devices can be used in the system 100 for a variety of differing functions. Thus, multiple measurement devices may be used.

In some examples, the measurement device is one or more cameras for capturing live images and may be combined with the camera(s) 120, or replaced by the camera(s) 120.

Examples of the measurement device(s) 102 can include a 3D laser scanner attached to a robotic arm, a portable coordinate measuring machine, or a portable handheld laser scanner.

The measurement device(s) 102 may be a wireless device or a wired device, such as a hand held device or attached by an articulating arm to obtain a view of the bone. In further examples, the measurement device(s) 102 may include an ultrasonic sensor to register the bone before an initial incision.

The measurement device(s) 102 collects information about the patient and sends the information to the computing device 104.

The computing device 104 includes processor(s) 106, and data storage 108 including instructions 110 executable by the processor(s) 106 for performing functions, an input interface 112, and an output interface 114 each connected to a communication bus 116. The computing device 104 may also include hardware to enable communication within the computing device 104 and between the computing device 104 and other devices (not shown). The hardware may include transmitters, receivers, and antennas, for example.

The processor(s) 106 may be a general-purpose processor or a special purpose processor (e.g., digital signal processors, application specific integrated circuits, etc.). The processor(s) 106 may receive inputs from the data storage 108 and the input interface 112, and process the inputs to generate outputs that are stored in the data storage 108 and output to the output interface 114. The processor(s) 106 can be configured to execute the executable instructions 110 (e.g., computer-readable program instructions) that are stored in the data storage 108 and are executable to provide the functionality of the system 100 described herein.

The data storage 108 may include or take the form of one or more computer-readable storage media that can be read or accessed by the processor(s) 106. The computer-readable storage media can include volatile and/or non-volatile storage components, such as optical, magnetic, organic, semiconductor-based or other memory or disc storage, which can be integrated in whole or in part with the processor(s) 106. The data storage 108 is considered non-transitory computer readable media. In some embodiments, the data storage 108 can be implemented using a single physical device (e.g., one optical, magnetic, organic or other memory or disc storage unit), while in other embodiments, the data storage 108 can be implemented using two or more physical devices.

The data storage 108 thus is a non-transitory computer readable storage medium, and executable instructions 110 are stored thereon. The instructions 110 include computer executable code. When the instructions 110 are executed by the processor(s) 106, the processor(s) 106 are caused to perform functions. Such functions include determining a visual model of a bone of a patient based on information collected by the measurement device(s) 102 and/or the camera 120, recognizing a position and a movement of the bone in physical space based on tracked reference points, recognizing a position and a movement of a surgical device in physical space based on tracked reference points, and providing for display a virtual image overlaid onto the visual model of the bone, for example.

The input interface 112 may be a wireless interface and/or one or more wireline interfaces that allow for both short-range communication and long-range communication to one or more networks or to one or more remote devices. Such wireless interfaces may provide for communication under one or more wireless communication protocols, such as Bluetooth, WiFi (e.g., an institute of electrical and electronic engineers (IEEE) 802.11 protocol), Long-Term Evolution (LTE), cellular communications, near-field communication (NFC), and/or other wireless communication protocols. Such wired interfaces may include data buses such as Ethernet interface, a Universal Serial Bus (USB) interface, or similar interface to communicate via a wire, a twisted pair of wires, a coaxial cable, an optical link, a fiber-optic link, or other physical connection to a wireline network. Thus, the input interface 112 may be configured to receive input data from the measurement device(s) 102 and the camera(s) 120, and may also be configured to send output data to other devices.

The output interface 114 outputs information to the display 118 or to other components as well. Thus, the output interface 114 may be similar to the input interface 112 and can be a wireless interface (e.g., transmitter) or a wired interface as well.

The display 118 may be a stand-alone display or incorporated within the computing device 104.

The camera(s) 120 may include a dedicated high resolution camera array for real time tracking and augmented reality. As an example, the camera(s) 120 may include two cameras or stereo cameras for 3D vision applications. The cameras 120 will also be able to collect measurement information to track surgical objects. Further, the cameras 120 can obtain depth measurements and calculate distance measurements using a stereo camera array. Within examples below, the camera(s) 120 collect images and/or other data to track objects in real time. For example, the camera(s) 120 may be used together with the measurement device(s) 102 to track objects such as to acquire intraoperative data, or the camera(s) 120 may perform the real time tracking of the bones, surgical devices, etc. themselves. The camera(s) 120 output image data to the input interface 112.

Figure 2:
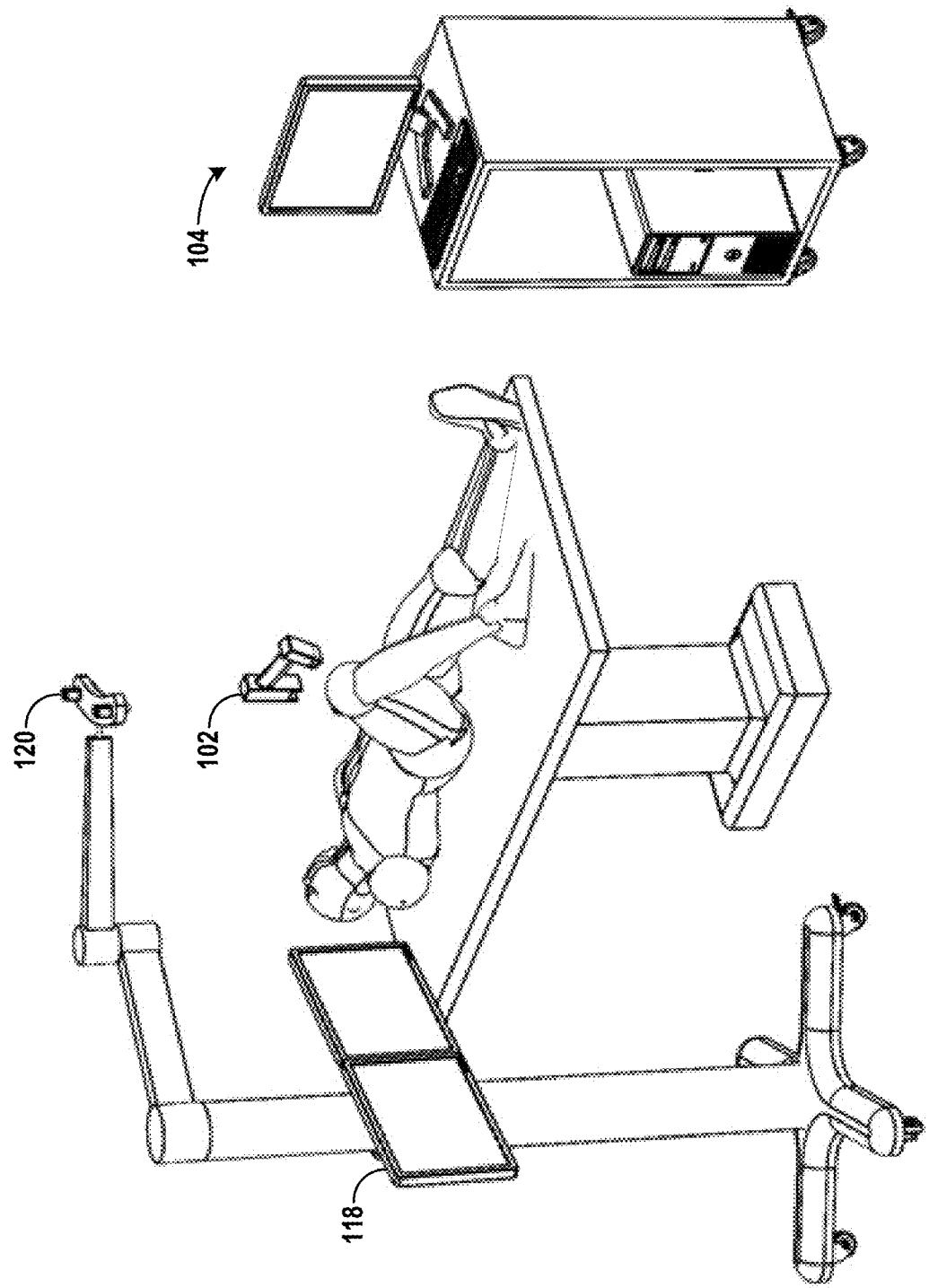
FIG. 2 is a representation of the system in an operating room, according to an example embodiment.

FIG. 2 is a representation of the system 100 in an operating room, according to an example embodiment. The measurement device 102 is shown as a handheld device to scan a bone of the patient. The computing device 104 is shown as a traditional desktop computer with display, and the display 118 is shown mounted on a standing mount such that the surgeon can easily visualize the screen during surgery. The camera(s) 120 are mounted overhead to capture a birds-eye-view of the patient and surgery.

A surgeon may operate the measurement device(s) 102 as a handheld 3D laser scanner to pass the measurement device(s) 102 over the bone undergoing surgery and/or other anatomy of the patient to collect information and learn geometry of the bone with the laser. The information may be point-cloud data about a surface of the bone of a limb of the patient, for example, that can be used by the processor(s) 106 to determining a visual model of the bone.

The measurement device(s) 102 may be used during surgery so as to collect the information of the surface of the bone as exposed from the limb of the patient in real time during surgery, and the processor(s) perform functions to determine the visual model of the bone intraoperatively during surgery. Thus, surgery may begin and the bone can be exposed, and following, a surface of the bone can be scanned by the measurement device(s) 102 to create a visual model of the bone in real time during surgery. As a specific example for a knee surgery, once the distal end of the femur and tibia are exposed to the greatest degree during surgery, the bone will be registered into the system 100. Registration of the bone can occur entirely intraoperatively to provide the most up to date and accurate data of the anatomy of the patient.

In other examples, the measurement device(s) 102 may be used prior to surgery to collect pre-operative imaging of at least a portion of the limb of the patient. In this example, pre-operative imaging can include, but is not limited to, CT scans, Mill, x-rays, etc., used to construct a preoperative 3D model. Once the pre-operative images are obtained, the pre-operative imaging can be aligned with the collected information of the surface of the bone obtained during surgery to further determine the visual model of the bone based on the aligned pre-operative imaging with the collected information of the surface of the bone. Geometry from the pre-operative imaging can be matched with geometry of actual anatomy of the patient by performing point cloud analysis and imaging matching. Intraoperative data can thus be used to align preoperative data to remove a process of using a touch probe to identify landmarks to align preoperative data. The processor(s) 106 can provide for display the pre-operative image on screen as well as the visual model created from the pre-operative imaging and information collected during surgery, and the images move on screen with movement of the leg of the patient as a result of optical tracking by the camera(s) 120.

Figure 3:
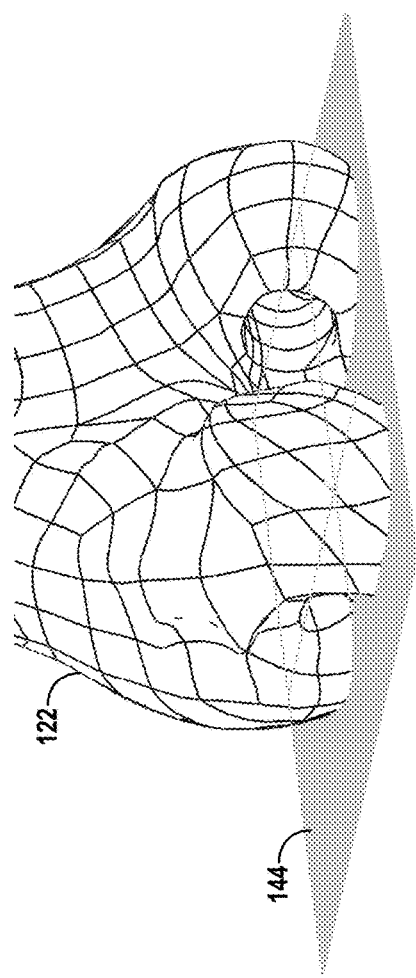
FIG. 3 illustrates an example visual model of a bone, according to an example embodiment.

FIG. 3 illustrates an example visual model 122 of a bone, according to an example embodiment. The visual model shows an outline of the bone in 3D to illustrate features of the bone.

In some other examples, the visual model 122 includes a live image of the bone rather than an outline or graphics.

The measurement device(s) 102 and/or the camera(s) 120 also track one or more reference points positioned on one or more bones or an anatomy of the patient, and the processor(s) 106 can recognize a position and a movement of the bone in physical space based on the tracked reference points positioned on the one or more of the bone or the anatomy of the patient and cause the visual model of the bone to reflect the position and the movement of the bone in physical space.

Figure 4:
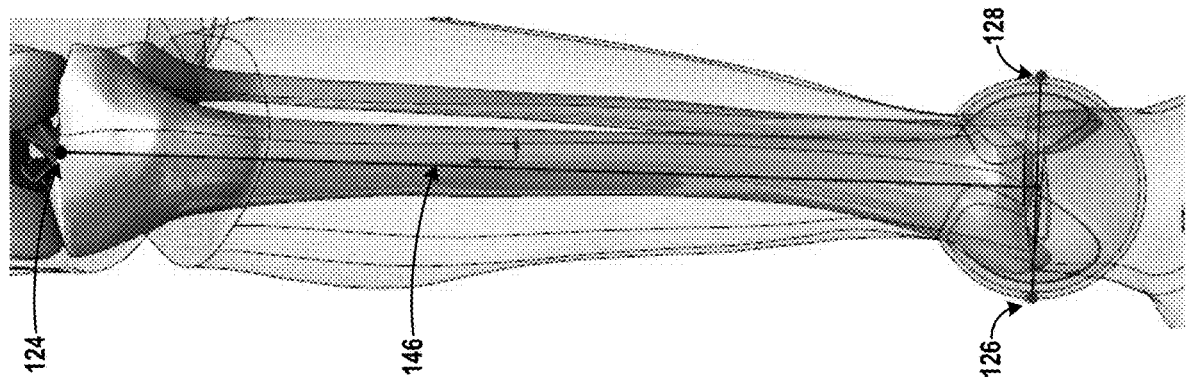
FIG. 4 illustrates a conceptual portion of a limb of a patient with reference points positioned on the bone for tracking, according to an example embodiment.

FIG. 4 illustrates a conceptual portion of a limb of a patient with reference points 124, 126, and 128 positioned on the bone for alignment and/or tracking, according to an example embodiment. The reference points 124, 126, and 128 may be physical objects positioned on the bone at certain positions, or virtual reference points assigned to certain positions on the bone that can be recognized in three dimensional space. The measurement device(s) 102 and/or the camera(s) 120 tracks the reference points 124, 126, and 128 by continuously taking measurements during surgery to identify movement of the bone, and provides information of movement of the bone to the processor(s) 106. The processor(s) 106 can update a viewpoint of the visual model of the bone to reflect the position and the movement of the bone in physical space. In this way, the surgeon will have a visual model of the bone on the display 118 that accurately reflects the position of the bone during surgery.

Thus, during surgery and after the exposed bone and leg is registered into the system 100, the surgeon may place the reference points 124, 126, and 128 that will act as an array onto the bone that was just registered, as well as on any other locations on the anatomy of the patient as desired. The reference points 124, 126, and 128 may be virtual reference points. In another example, physical reference points can be attached to the patient through adhesive properties, marking or coloring the patient, pinning the reference points, and other techniques as well. These points will act as an array and can be used by the measurement device(s) 102 to recognize where the bone is in relation to the visual model 122 for the registered bone. Then the data for the registered bone will be referenced virtually to the actual patient's bone in real time as the bone moves. The leg will be moved around in various ways to track movement of this virtual or physical reference point(s). The measurement device(s) 102 and/or the camera(s) 120 can be used to track the motion of the virtual reference point(s) and the patient's leg.

The measurement device(s) 102 and/or the camera(s) 120 can track reference points positioned on any number of areas of the bone and/or the anatomy of the patient, including on one or more of a distal anterior tibial crest of the patient, a medial malleoli of the patient, a lateral malleoli of the patient, a reference off a medial third or other portion of the tibial tubercle of the patient, a base of an anterior cruciate ligament of the patient, and a posterior cruciate ligament and intercondylar eminences of the patient, for example. In addition, such reference points positioned in these areas can be used to identify mechanical axes or align preoperative scan data, as discussed more fully below.

In another example, to recognize the position and the movement of the bone in physical space, tracked reference points positioned on a positioning device can be determined. For example, a portion of the limb of the patient or a foot of the patient can be rigidly positioned within the positioning device, and the measurement device(s) 102 and/or the camera(s) 120 track a reference point positioned on the positioning device. The processor(s) then can determine the position and movement of the bone from the tracked positioning device due to alignment of the limb of the patient or the foot of the patient within the positioning device. With the foot correctly aligned in the positioning device, the measurement device(s) 102 and/or the camera(s) 120 track the positioning device to determine movement. In some examples, it can be difficult to track movement of the bone or foot itself, and so the positioning device can be used to hold the foot rigidly, and tracked to avoid putting pins in bone to hold in place.

The measurement device(s) 102 and/or the camera(s) 120 also track one or more reference points positioned on a surgical device, and the processor(s) 106 recognizing a position and a movement of the surgical device in physical space based on the tracked reference points positioned on the surgical device.

Figure 5:
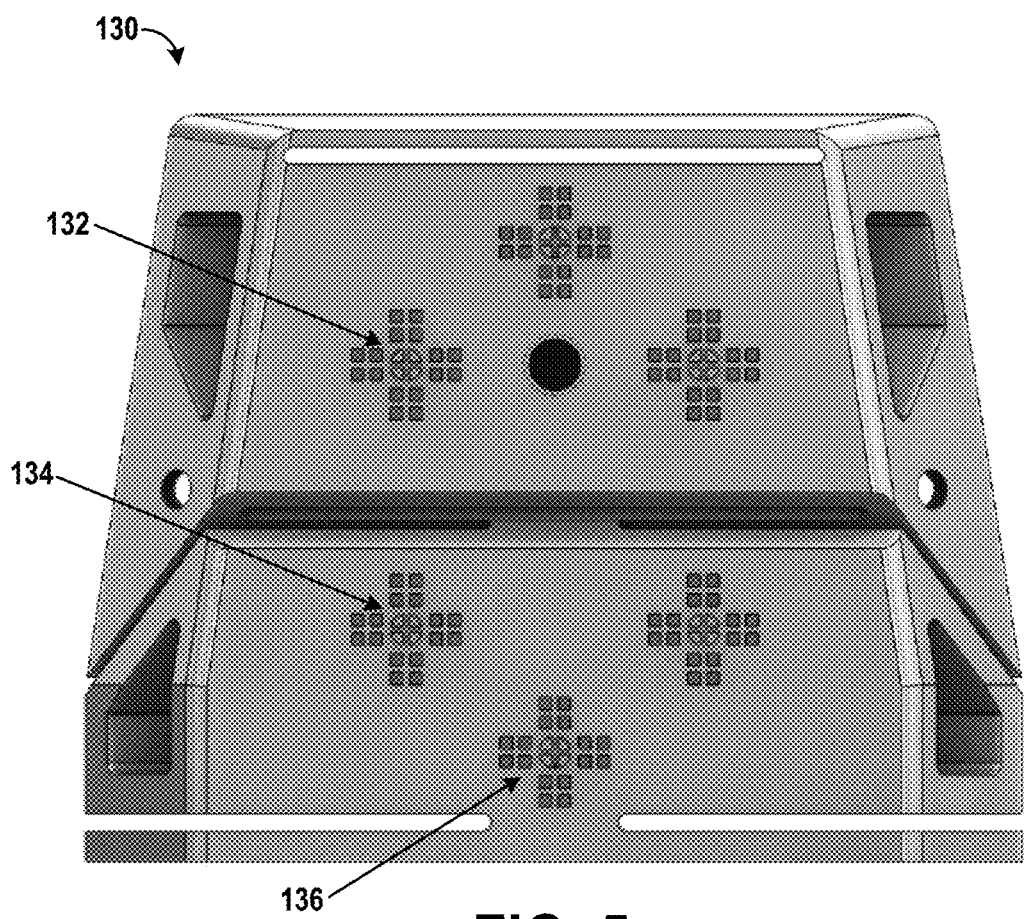
FIG. 5 illustrates an example surgical device, according to an example embodiment.
Figure 6:
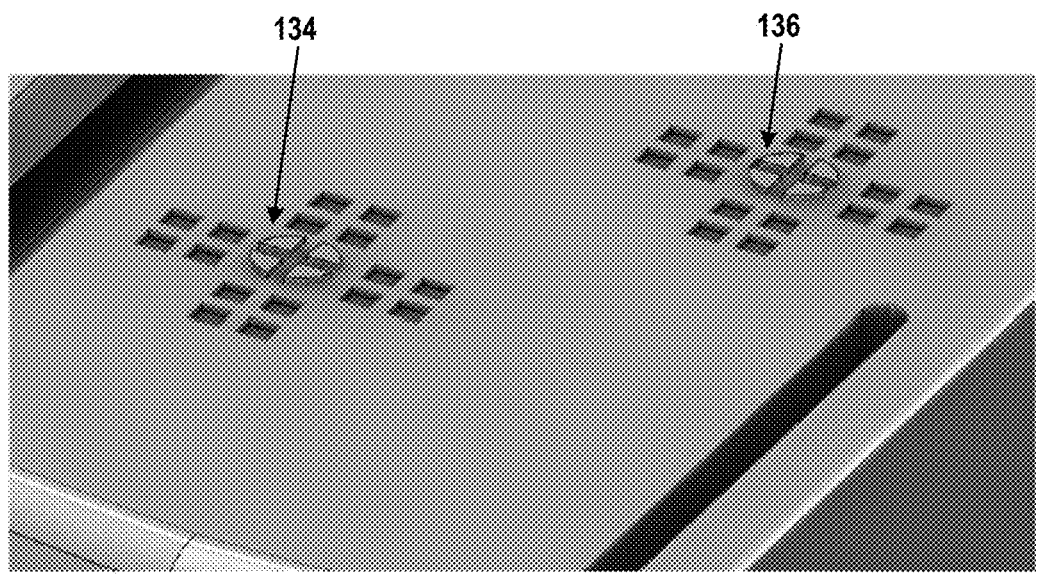
FIG. 6 illustrates another view of the example surgical device, according to an example embodiment.

FIG. 5 illustrates an example surgical device 130, according to an example embodiment. FIG. 6 illustrates another view of the example surgical device 130, according to an example embodiment. The surgical device 130 shown in FIG. 5 is a cut guide, and reference points are included on a surface of the cut guide that can be tracked by the measurement device(s) 102 and/or the camera(s) 120. Example reference points include reference points 132, 134, and 136. The measurement device(s) 102 and/or the camera(s) 120 track the reference points 132, 134, and 136 by taking continuous measurements during surgery to identify movement of the surgical device 130, and provides information of movement of the surgical device 130 to the processor(s) 106. The processor(s) 106 can update a viewpoint of the surgical device to reflect the position and the movement of the surgical device in physical space. In this way, the surgeon can have a visual view of the surgical device 130 on the display 118 that accurately reflects the position of the surgical device 130 during surgery.

After all the data above is collected, the measurement device(s) 102 and/or the camera(s) 120 will track the motion of the surgical device 130 as the surgeon moves the surgical device 130. The processor(s) 106 may receive the data and information collected and output by the measurement device(s) 102 and provide for display a virtual image overlaid onto the visual model 122 of the bone. The virtual image may be or include many items, and generally, includes information for assistance of placement of the surgical device 130 at a position on the bone based on the position and the movement of the surgical device 130 in physical space.

Figure 7:
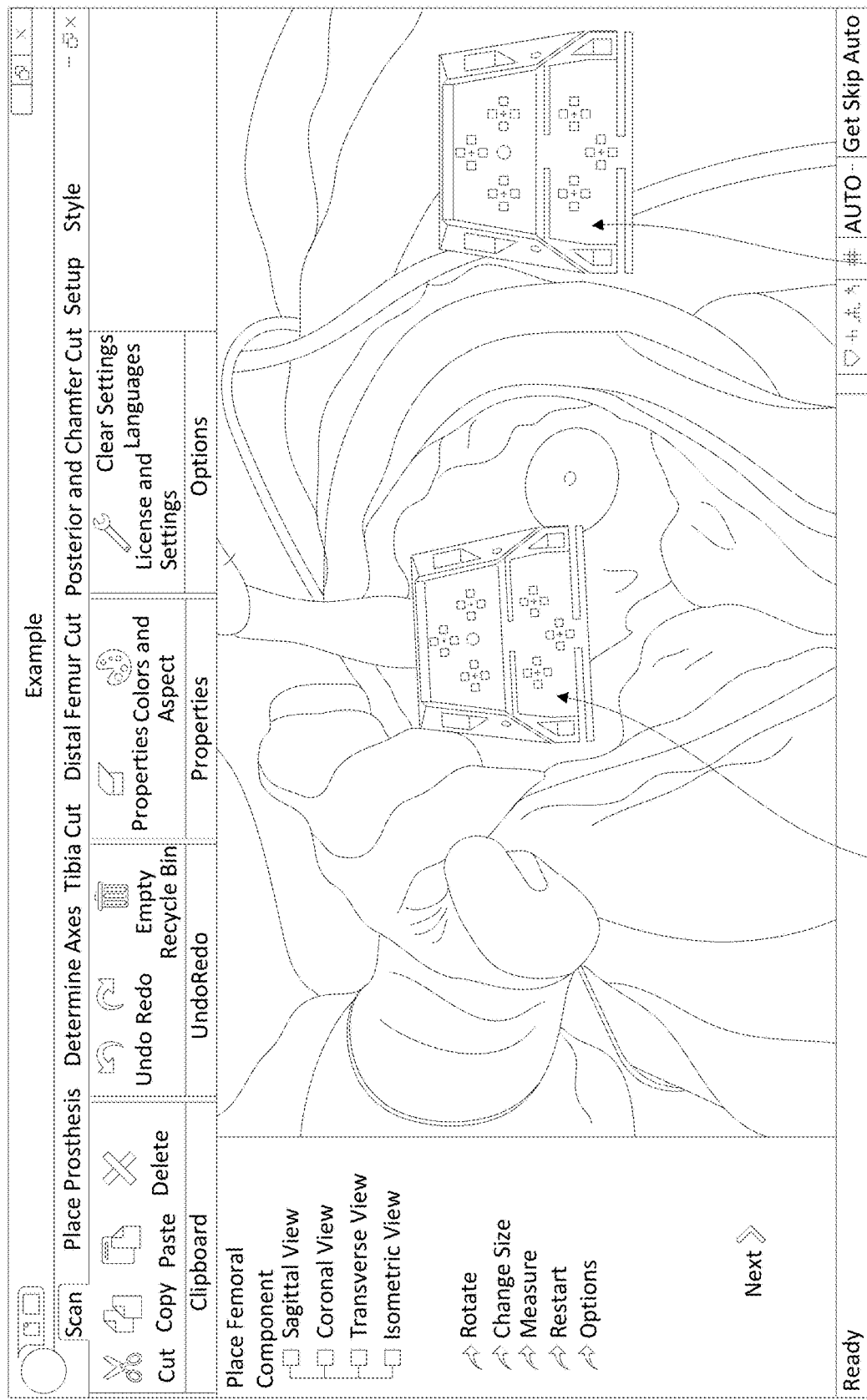
FIG. 7 is a conceptual illustration of a virtual image overlaid onto a visual model, according to an example embodiment.

FIG. 7 is a conceptual illustration of a virtual image overlaid onto a visual model, according to an example embodiment. The visual model in FIG. 7 includes a live image 138 of the bone exposed during surgery, and a virtual image 140 is illustrated overlaid onto the live image 138 of the bone showing cut guide positioning. The virtual image 140 includes a graphic of a cut guide and illustrates suggested placement that can be calculated based on many factors, for example, and data collected by the measurement device(s) 102 and/or the camera(s) 120, such that the graphic of the cut guide represents a real cut guide 142 as will physically be in the operating room. Details of placement of the virtual cut guide 140 are further described below. The graphic of the virtual image 140 may initially be red (or some color to indicate an incorrect position of the cut guide 142), and the graphic can change colors, such as to turn green when the surgeon has positioned the cut guide 142 in the correct position.

Thus, the camera(s) 120 can capture the live image 138 of the bone during surgery, and the processor(s) 106 can further provide for display the virtual image 140 overlaid on the live image 138 of the bone.

Referring back to FIGS. 3 and 4, a cut plane 144 can be determined, and provided for display as a virtual cutting plane onto the live image 140 of the bone. To determine the cut plane, initially, an axis of the limb is determined.

Figure 8:
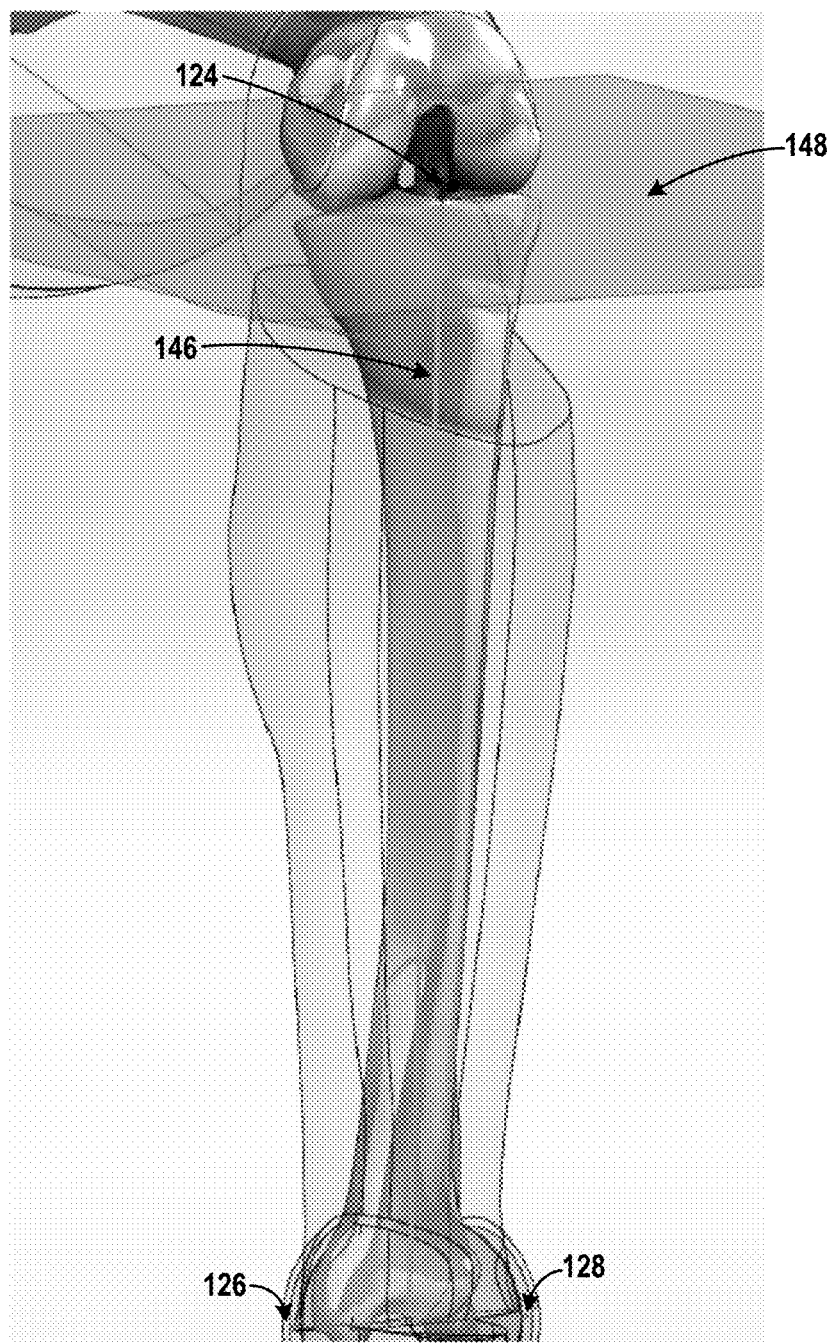
FIG. 8 illustrates a conceptual portion of a limb of a patient as in FIG. 4 with a plane shown, according to an example embodiment.

FIG. 8 illustrates a conceptual portion of a limb of a patient as in FIG. 4 with a plane shown, according to an example embodiment. The reference points 124, 126, and 128 are used to calculate a mechanical axis of the limb. Reference points 126 and 128 will be on each side of the malleoli, and reference point 124 will be on the anterior cruciate ligament (ACL) footprint, as shown in FIG. 4. A midpoint between reference points 126 and 128 can be calculated, and then a line 146 between the midpoint and the reference point 124 will be the mechanical axes for the tibia. From reference point 124 and the mechanical axis line, a plane 148 can be made coincident with reference point 124 and perpendicular to the mechanical axis line 146. Then the cut plane 144 can be created by offsetting from the plane 148 by a distance specified by a size of the implant selected by the surgeon (10 mm or 11 mm, for example), as shown in FIG. 3.

Thus, within examples, the processor(s) 106 can determine the axis 146 of the limb based on reference points positioned on a medial malleoli of the patient, a lateral malleoli of the patient, and a base of an anterior cruciate ligament of the patient, and provide the axis 146 of the limb for display. The processor(s) 106 determine a median point between a medial malleoli of the patient and a lateral malleoli of the patient, and determining a virtual line from the median point up to a point at the base of the ACL of the patient. The processor(s) 106 can also calculate the axis 146 of the limb based on the visual model 122 and the position and the movement of the bone in physical space, and the axis can include one of a mechanical axis, a kinematic axis, or an anatomical axis. In some examples, however, implant placement can be assessed without a need to calculate a mechanical axis, such as, assessing implant placement using only information from the registered bone surface(s).

Figure 9:
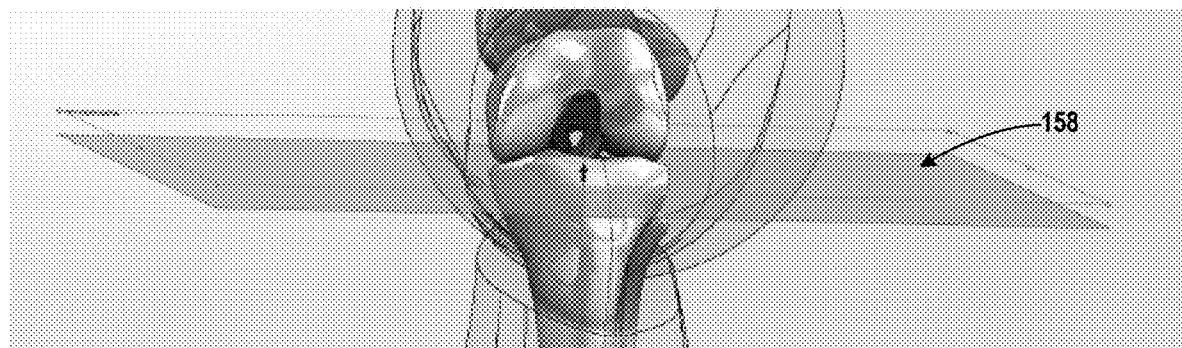
FIG. 9 illustrates a conceptual portion of a limb of a patient with a plane shown, according to an example embodiment.
Figure 10:
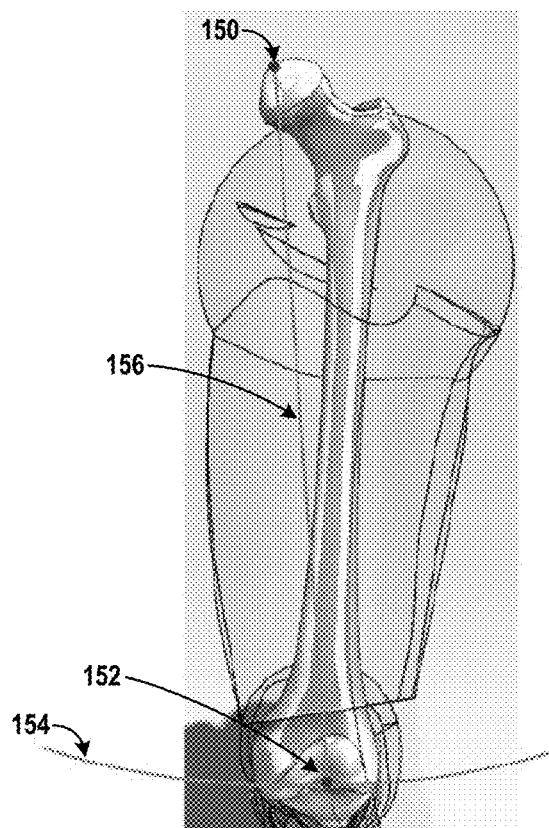
FIG. 10 illustrates a conceptual portion of a limb of a patient with a mechanical axis shown, according to an example embodiment.

FIG. 9 illustrates a conceptual portion of a limb of a patient with a plane shown, and FIG. 10 illustrates a conceptual portion of a limb of a patient with a mechanical axis shown, according to an example embodiment. In this example, for the femur, point 152 (virtual or physical) will be placed on the exposed distal femur. The surgeon will rotate the patient's right or left leg and a position of the point 152 will be tracked. A plurality of points in addition to point 152 could be placed physically or virtually on the distal portion of the femur and tracked by the measurement device(s) 102 and/or the camera 120. A center of rotation can be determined as the point about which the distal femur rotates, generating an arc, a spherical segment, a cap, or a dome 154, and the center point of which is a center of hip rotation noted as point 150 in FIG. 10. Then a line 156 from the point at the center of rotation to the placed point(s) will be the mechanical axis, and a plane 144 can be determined as discussed above. The plane 144 is shown in FIG. 3.

Thus, the axis of the limb can be calculated based on extrapolating a point of rotation of a hip of the patient during movement of the limb based on tracked reference points positioned on a distal end of a femur, and the virtual line 156 from the point of rotation of the hip up to a point at the base of the ACL of the patient can be determined.

As another example, the axis of the limb can be calculated based on data of an ankle of the patient, and peaks of sides of the ankle can be determined from at least two reference points. A median point between the peaks of the ankle is determined, and a virtual line from the median point up to a point at the base of the ACL of the patient is determined as the axis.

Within examples, because the cut guide 142 has a known cutting plane through the bone associated with it (referenced from an angle of slot(s) in the cut guide), as the cut guide 142 moves around in reference to the bone, cut plane(s) can be displayed on the screen on the image of the registered bone. An example cut plane is shown in FIG. 3 as the cut plane 144 that illustrates the projected cut plane generated from the physical cut guide. The plane 144 moves around in the simulated view based on where the surgeon moves the physical cut guide on the patient's anatomy. This will give the surgeon a virtual view of how the resections on the bone would look before the surgeon physically makes the cut. Thus, the processor(s) 106 may further provide a virtual view of a resection on the bone for display.

Augmented reality may also be used to overlay the virtual cut planes 144, 148, and 158 onto the live image 138 of the patient's exposed femur and tibia. This augmented reality view could also combine aspects of the visual model 122 of the bone with a live view to generate the best suited view for the surgeon.

In some examples, the surgeon is able to virtually place a tibial and femoral prosthesis intraoperatively on top of the visual model 122 of the registered bone. Various views, such as sagittal, coronal, transverse, or isometric views of the modeled bone can be selected. The visual model 122 can be manipulated to a custom view to place the virtual prosthesis.

Figure 11:
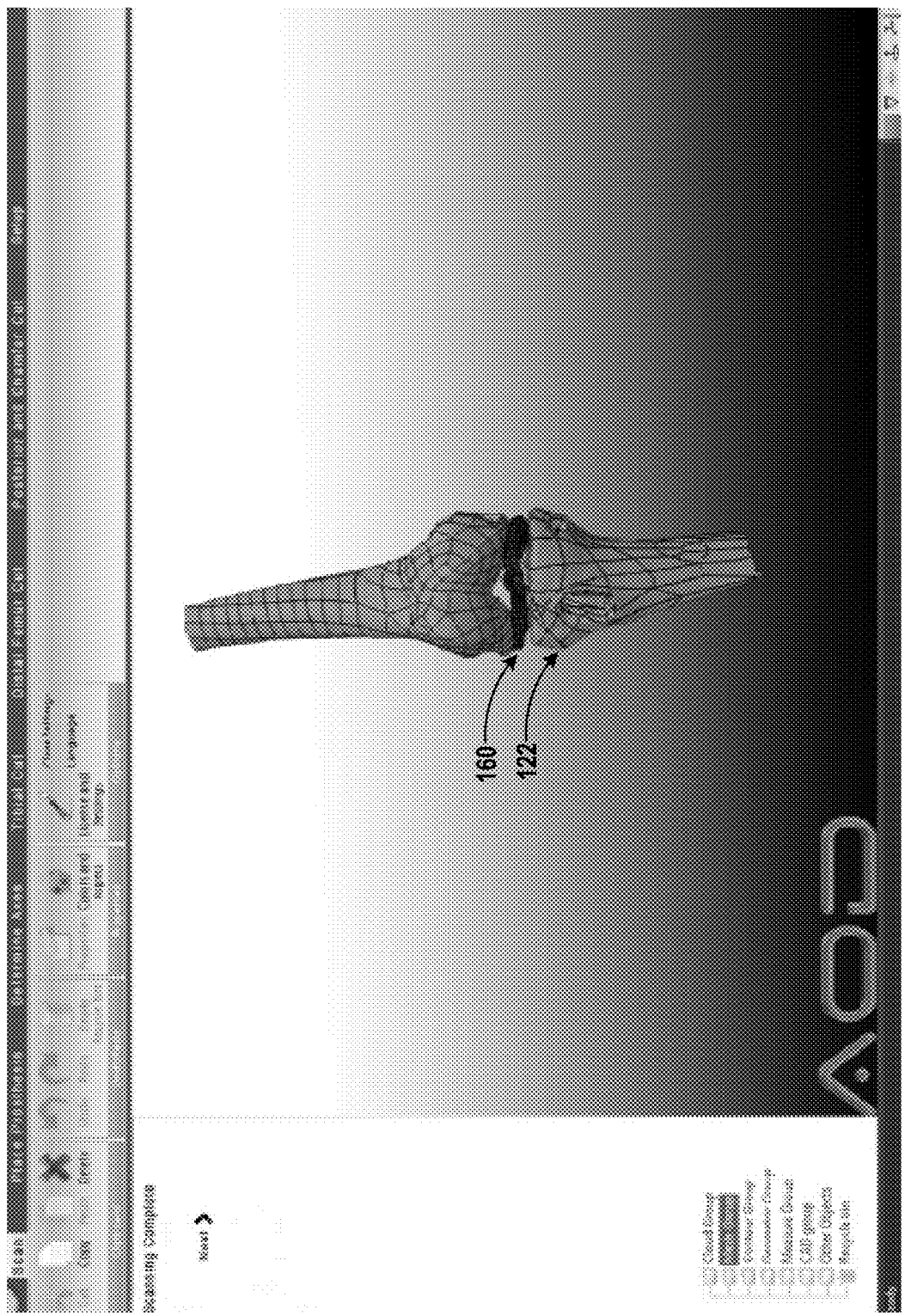
FIG. 11 illustrates a conceptual portion of the visual model of a limb of a patient with a prosthesis inserted, according to an example embodiment.

FIG. 11 illustrates a conceptual portion of the visual model 122 of a limb of a patient with a component(s) of the prosthesis 160 inserted, according to an example embodiment. The prosthesis 160 is shown as a graphic illustrating placement of the prosthesis 160 in relation to the bone.

Figure 12:
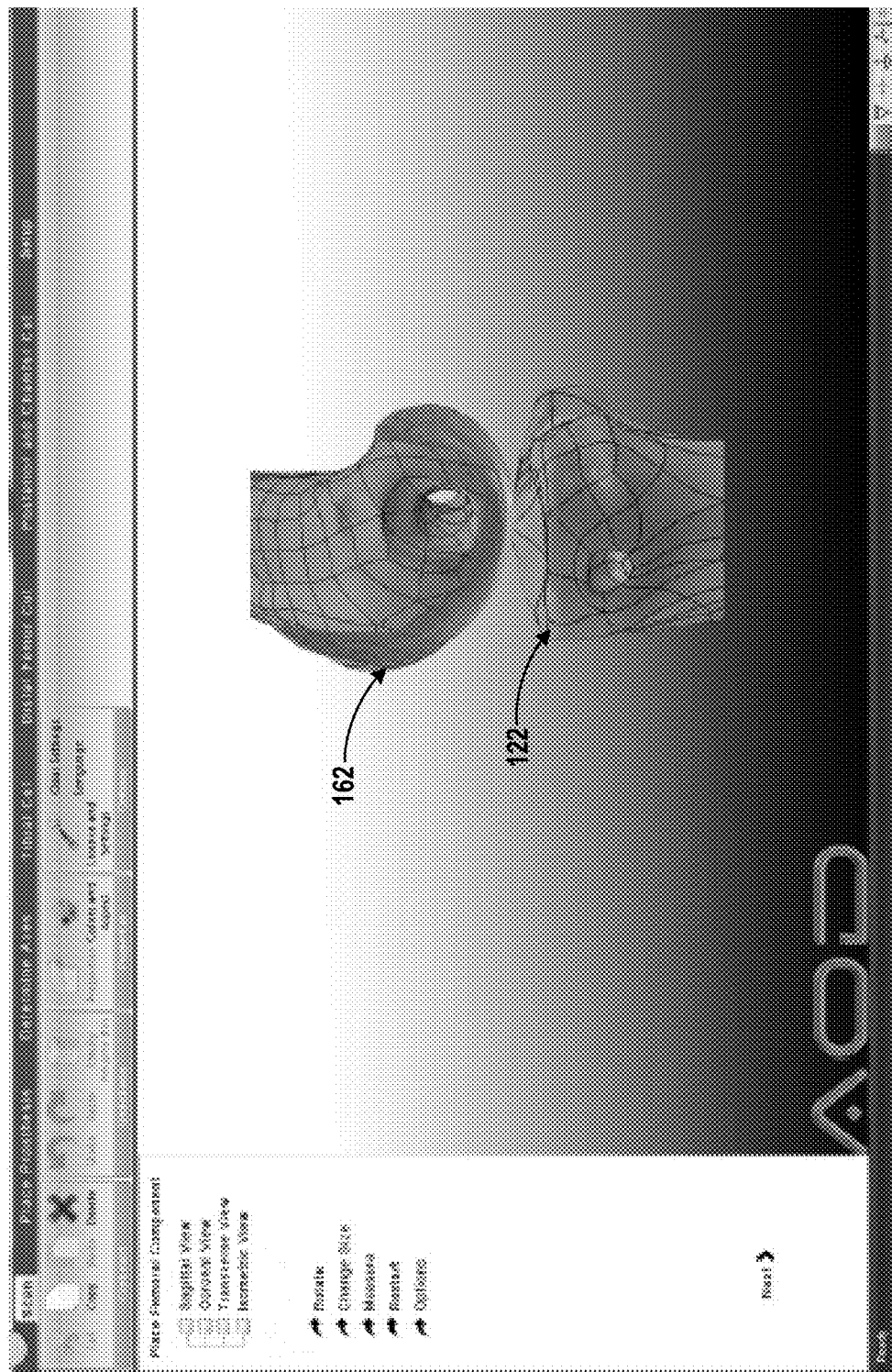
FIG. 12 illustrates a conceptual portion of the visual model of a limb of a patient with another prosthesis inserted, according to an example embodiment.

FIG. 12 illustrates a conceptual portion of the visual model 122 of a limb of a patient with another prosthesis 162 inserted, according to an example embodiment. In one example, since geometry of the prosthesis 162 matches with the plane(s) of the cut guides and all the geometry of the cut guides are known, the processor(s) 106 will calculate where the cut guides will need to be placed in order for the prosthesis 162 to be positioned where the surgeon virtually placed the prosthesis 162. The measurement device(s) 102 and/or the camera(s) 120 will track motion of the cut guide in real time using, but not limited to, a tracking pattern on the back of each cut guide as described above, to match the cut guide to the known geometry of that specific cut guide. The surgeon my use a cut guide positioning apparatus, and the processor(s) 106 illustrate information for the surgeon to use to adjust the cut guide into place, so that the cut guides will produce a geometry that match the surgeon's virtual placement of the prosthesis 162.

Figure 13:
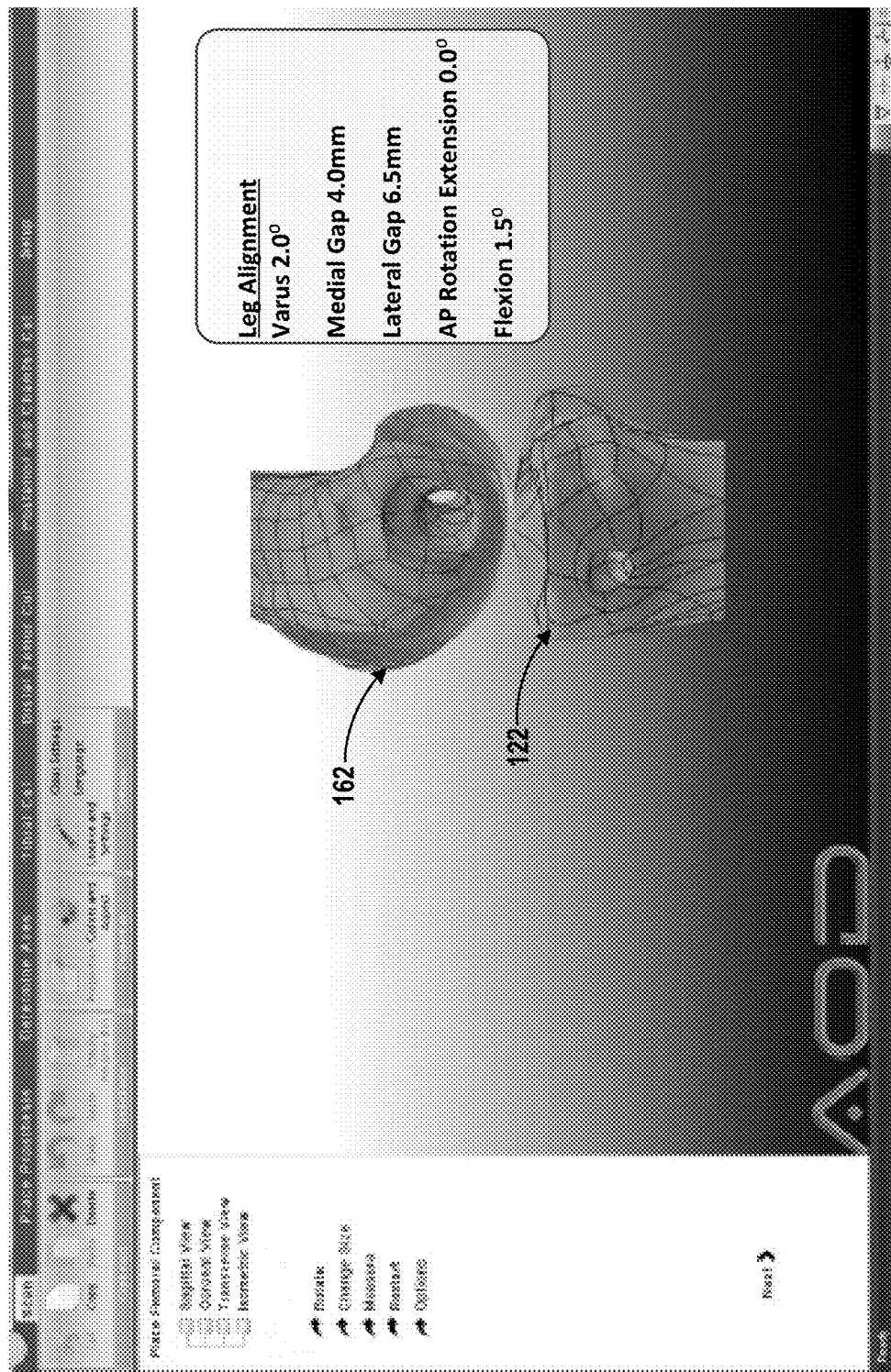
FIG. 13 illustrates a conceptual image of placement of a prosthesis and additional data to be displayed, according to an example embodiment.

FIG. 13 illustrates a conceptual image of placement of a prosthesis 164 and additional data to be displayed, according to an example embodiment. Such additional data may include one or more of a lateral gap of a knee of the patient, a medial gap of the knee of the patient, a varus and/or valgus alignment of the knee of the patient, a degree of flexion of a femoral cut, a slope of a tibial cut (e.g., tibial plateau cut), and an anteroposterior (AP) rotation extension.

Thus, as shown in FIG. 13, alongside the visual representation, information such as, but not limited to, lateral gap, medial gap, valgus alignment, flexion, and/or AP rotation extension as the information relates to the cut being made can be displayed. The measurement device(s) 102 and/or the camera(s) 120 will track the motion of the cut guide in real time using, but not limited to, a tracking pattern on the back of the cut guide or using measurement to match the cut guide to the known geometry of that specific cut guide, and the surgeon may either move the cut guide around freely or have the cut guide attached to a refined positioning system that would be attached to the patient. This cut guide positioning apparatus would be able to finely adjust the cut guides along the X, Y, and Z axes as well as the pitch, roll, and yaw. The measurement device(s) tracks a position of the guide positioning device as well.

Within examples above, any number of combination of information may be displayed, and a specific example includes displaying the virtual image including placement of the surgical device as shown in FIG. 7, and a graphic illustrating placement of a prosthesis in relation to the bone and information indicating one or more of a lateral gap, a medial gap, and a valgus alignment of a knee of the patient with placement of the prosthesis, as shown in FIG. 13.

Once the tibial and femoral prosthesis are in place, a position of the prosthesis can be verified with the measurement device(s) 102 and/or the camera(s) 120 to verify that the prosthesis was placed in the correct position. The post placement verification will also provide useful metrics that will denote success of the surgery, including but not limited to, lateral gap, medial gap, valgus alignment, flexion, or AP rotation extension. Thus, the measurement device(s) 102 and/or the camera(s) 120 may further scan or measure a prosthesis after placement in the bone and output prosthesis data, and the processor(s) 106 verifies placement of the prosthesis in the bone to a determined position based on the prosthesis data. The method can be repeated in part or in whole if the prosthesis is not positioned correctly according to the system or based on the judgement of the surgeon.

Figure 14:
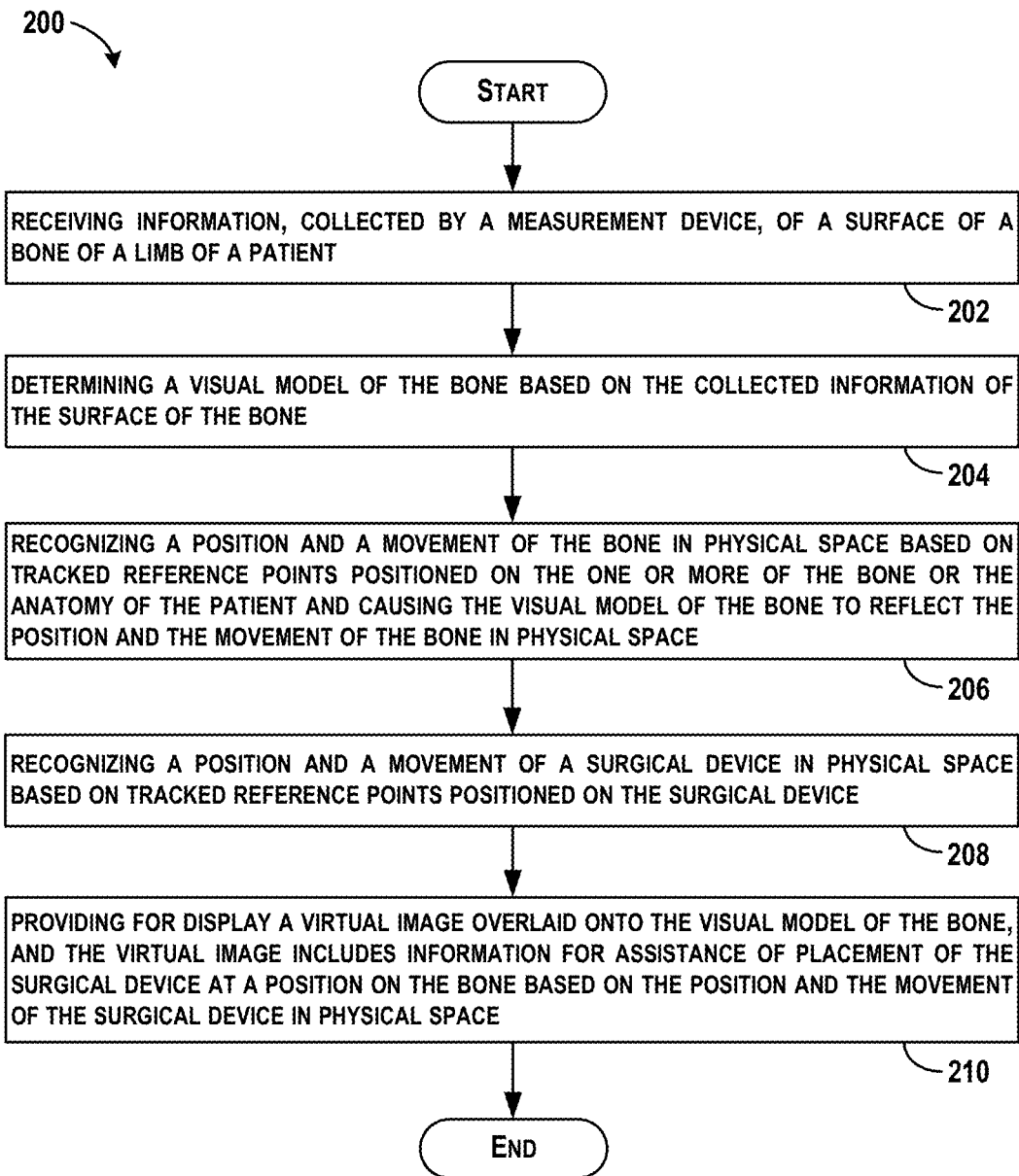
FIG. 14 shows a flowchart of an example method for determining and providing for display a virtual image overlaid onto a visual image of a bone, according to an example embodiment.

FIG. 14 shows a flowchart of an example method 200 for determining and providing for display a virtual image overlaid onto a visual image of a bone, according to an example embodiment. Method 200 shown in FIG. 14 presents an embodiment of a method that could be used with the system 100 shown in FIG. 1 and the computing device 104 shown in FIG. 2, for example. Further, devices or systems may be used or configured to perform logical functions presented in FIG. 14. In some instances, components of the devices and/or systems may be configured to perform the functions such that the components are actually configured and structured (with hardware and/or software) to enable such performance. In other examples, components of the devices and/or systems may be arranged to be adapted to, capable of, or suited for performing the functions, such as when operated in a specific manner. Method 200 may include one or more operations, functions, or actions as illustrated by one or more of blocks 202-210. Although the blocks are illustrated in a sequential order, these blocks may also be performed in parallel, and/or in a different order than those described herein. Also, the various blocks may be combined into fewer blocks, divided into additional blocks, and/or removed based upon the desired implementation.

It should be understood that for this and other processes and methods disclosed herein, flowcharts show functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer readable medium or data storage, for example, such as a storage device including a disk or hard drive. Further, the program code can be encoded on a computer-readable storage media in a machine-readable format, or on other non-transitory media or articles of manufacture. The computer readable medium may include non-transitory computer readable medium or memory, for example, such as computer-readable media that stores data for short periods of time like register memory, processor cache and Random Access Memory (RAM). The computer readable medium may also include non-transitory media, such as secondary or persistent long term storage, like read only memory (ROM), optical or magnetic disks, compact-disc read only memory (CD-ROM), for example. The computer readable media may also be any other volatile or non-volatile storage systems. The computer readable medium may be considered a tangible computer readable storage medium, for example.

In addition, each block in FIG. 14 may represent circuitry that is wired to perform the specific logical functions in the process. Alternative implementations are included within the scope of the example embodiments of the present disclosure in which functions may be executed out of order from that shown or discussed, including substantially concurrent or in reverse order, depending on the functionality involved, as would be understood by those reasonably skilled in the art.

At block 202, the method 200 includes receiving information, collected by the measurement device(s) 102 and/or the camera(s) 120, of a surface of a bone of a limb of a patient.

At block 204, the method 200 includes determining the visual model 122 of the bone based on the collected information of the surface of the bone.

At block 206, the method 200 includes recognizing a position and a movement of the bone in physical space based on tracked reference points positioned on the one or more of the bone or the anatomy of the patient and causing the visual model of the bone to reflect the position and the movement of the bone in physical space. Position coordinates of the tracked reference points can be determined referenced to the measurement device(s) 102 and/or the camera(s) 120 performing the tracking.

At block 208, the method 200 includes recognizing a position and a movement of a surgical device in physical space based on tracked reference points positioned on the surgical device.

At block 210, the method 200 includes providing for display a virtual image overlaid onto the visual model of the bone, and the virtual image includes information for assistance of placement of the surgical device at a position on the bone based on the position and the movement of the surgical device in physical space.

The method 200 may be performed in real time during surgery to collect the information of the surface of the bone as exposed from the limb of the patient. For example, the information can be received using measurement device(s) 102 and/or the camera(s) 120 in real time during surgery.

As described within examples above with respect to the system 100, the method 200 can include providing a virtual view of a resection on the bone, and can display the virtual image including placement of the surgical device, a graphic illustrating placement of a prosthesis in relation to the bone, and information indicating one or more of a lateral gap, a medial gap, and a valgus alignment of a knee of the patient with placement of the prosthesis.

In addition, as described within examples above with respect to the system 100, the method 200 can include calculating an axis of the limb based on the visual model and the position and the movement of the bone in physical space, and the axis is one of a mechanical axis, a kinematic axis, or an anatomical axis.

In an example method, virtual or physical points can be placed on the medial and lateral malleoli of the patient, along with the base of the ACL foot print of the tibia. The method 200 can be further executed to create a plane in space that is referenced off of the three reference points (as described above with respect to FIGS. 3, 4, and 8). This method will then show surgeons the mechanical axis plane of the tibia from the sagittal view. To create the mechanical axis line, the median distance between the two malleoli's can be interpreted, and a virtual line from the median line up to the point that sits at the ACL foot print can be determined. Once the mechanical axis is established, the cutting guide will be able to be adjusted in multiple different axes to create the proper resection, such as but not limited to, the posterior slope, height, and rotation. This can be accomplished by either having a supportive fixture that allows for adjustments of the cutting guide itself, or by having cut guides that contain mechanisms that allow for further adjustments once they have been pinned to the bone. The measurement device(s) 102 and/or the camera(s) 120 will be able to track the movement of the cutting guide by having reference points attached directly on the cutting guide, or by having a temporary insert that engage with the cut blocks with reference points. Once the correct position is met by image recognition (due to tracked reference points by the measurement device(s) 102 and/or the camera(s) 120), the surgeon can make the tibial plateau cut. In another instance, once the scan of the exposed tibia and the lower portion of the knee is acquired, the processor(s) 106 can calculate the peaks of both sides of the ankle from at least two planes, the sagittal and coronal, but not limited to. This can be an alternative method to calculate the midline between the medical and lateral malleoli, and have the processor(s) 106 draw a virtual line that connects the virtual midline from the patient's ankle up to the ACL footprint.

To create a sagittal cut or vertical cut for the tibial resections, additional instruments could be utilized to give surgeons a numerical value tied to dimensions of the tibia. In an example method, a probe can be used where one end has a hook or curve. The hooked end would engage with the posterior of the tibia and the system 100 can recognize the other end of the probe in relation to a metal cutting instrument or any other reference point to give the surgeon a numerical value of the total length of the tibial plateau.

In another example method for the sagittal cuts, the surgeon can also utilize a dual pronged probe that is of a certain fixed width. The surgeon would insert the fork into the patient's knee above the tibial plateau. The measurement device(s) 102 and/or the camera(s) 120 would recognize this specific instrument, and when the ends of the fork are in the midline, or a set distance in reference to the virtual point or physical point of the ACL footprint and the lateral or medial edge of the tibia, the measurement device(s) 102 and/or the camera(s) 120 would notify the surgeon and a measured sagittal resection can be made. This device can either be a standalone device, or be engaged or connected to the tibial cutting guide or any other fixed instrument.

In another example method, the exposed distal condyle of the femur is registered through the measurement device(s) 102 and/or the camera(s) 120, and the majority of the leg is also registered. A plurality of virtual or physical reference points can be placed on the femoral condyles, and used to calculate the center of the condyles. As the surgeon moves the hip the system 100 extrapolates the point of rotation by tracking the reference points on the distal end of the femur. Once the point of rotation is calculated, a virtual line can be created, which will be the mechanical axis, portions of which are shown and described above with reference to FIGS. 3 and 9-10, for example.

Example methods and systems described herein provide visual feedback to assist the surgeon in the placement of the cut guide or the prosthesis, and calculate measurement data to assist the surgery and provide real time data. The tracking of the bone and surgical devices with the spatial awareness to the bone to calculate the mechanical axes of the leg (without specifically identifying the endpoints of such mechanical axes, such as with a probe) is provided to assist the surgeon in placing the cut guides in the correct position onto the bone. Any number or array of measuring devices can be used to provide real time data as well as object tracking when the surgeon moves the cut guides, and the system 100 can further include augmented reality with the real time measurement array to assist the surgeon to place the cut guides by displaying the virtual cutting planes onto the live image of the bone in reference to the physical cut guide before the cut guide is fixed into place.

Example methods and systems described herein can be used during surgery, and generally, during any surgery, as a safety mechanism to prevent variation from a desired result. Example methods and systems described herein can manage variables and inform surgeons to place prostheses within a certain threshold of accuracy. Some example surgeries for use of the methods and systems include unicompartmental knee arthroplasty (UKA), total knee arthroplasty (TKA), total hip arthroplasty (THA), and resurfacing knee and hip arthroplasties.

Figure 15:
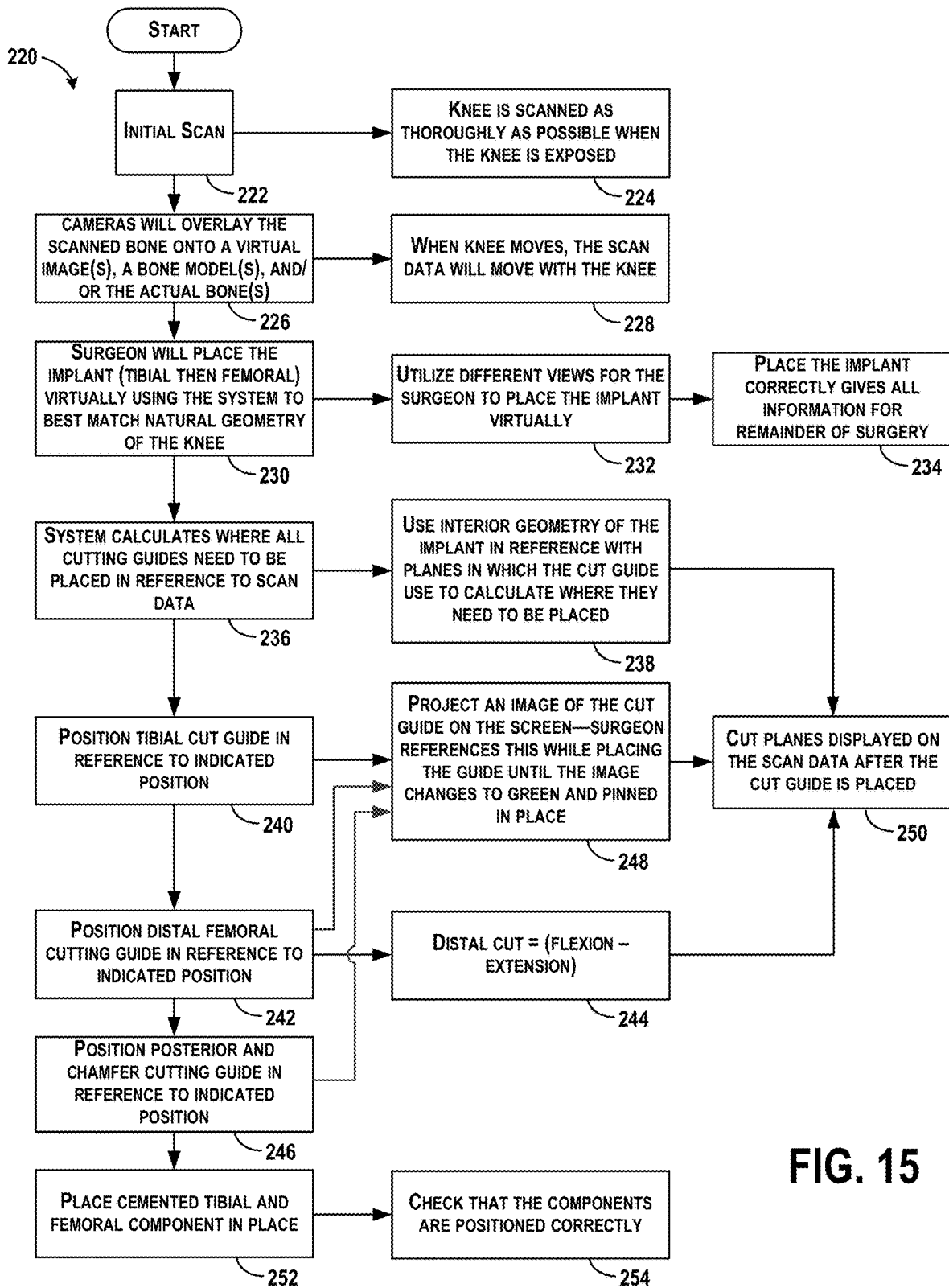
FIG. 15 shows a flowchart of another example method for positioning of a prosthesis, according to an example embodiment.

FIG. 15 shows a flowchart of another example method 220 for positioning of a prosthesis, according to an example embodiment. Initially, as shown at block 222, a scan of the bone or anatomy of the patient is performed (e.g., by the measurement device(s) 102). As shown at block 224, the knee is scanned as thoroughly as possible when the knee is exposed, for example.

Next, as shown at block 226, cameras will capture images and overlay the scanned bone onto the images of the actual bone, and as shown at block 228, when the knee moves (such as repositioning during surgery), the scan data will move with the knee. The augmented reality data includes a live direct or indirect view of a physical, real-world environment of the surgery whose elements are augmented (or supplemented) by computer-generated sensory input such as sound, video, or graphics data. In this example, the augmented reality will give the surgeon a real time view of the surgery with scanned data overlaid to help the surgeon precisely place the cut guides. The system may provide an augmented reality display including the live image of the bone in physical space supplemented by a computer-generated graphic of a cutting plane overlaid on the bone, for example.

Following, as shown at block 230, the surgeon will place the implant (tibial then femoral) virtually using the system to best match a natural geometry of the knee. As shown at block 232, different views can be utilized on the software to place the implant virtually, and as shown at block 234, once the implant is correctly positioned (within thresholds set for the surgery), the system can display information for a remainder of the surgery.

As shown at block 236, the system can calculate where all cutting guides need to be placed in reference to the scan data. At block 238, interior geometry of the implant is used in reference with planes in which the cut guide uses to calculate positioning of the cut guides.

At block 240, the surgeon positions the tibial cut guide in reference to the indicated positioned by the system. At block 242, the surgeon positions the distal femoral cutting guide in reference to the indicated position by the system. At block 244, the distal cut is shown to be equal to the posterior cut, which is equal to the flexion gap minus the tibial cut. At block 246, the surgeon positions the posterior and chamfer cutting guide in reference to the indicated position by the system. At block 248, the system projects an image of the cut guides on the screen, and the surgeon references this while placing the cut guides until the images on the screen change to green and the cut guides are pinned in place indicating correct positioning of the cut guides.

At block 250, the cut planes can be displayed by the system on the scan data after the cut guide is placed.

Following, at block 252, the surgeon places the cemented tibial and femoral component in place. At block 254, the positioning of the components is checked to verify correct placement. This may be accomplished by scanning the inserted components to match against the position indicated by the system, for example.

Figure 16:
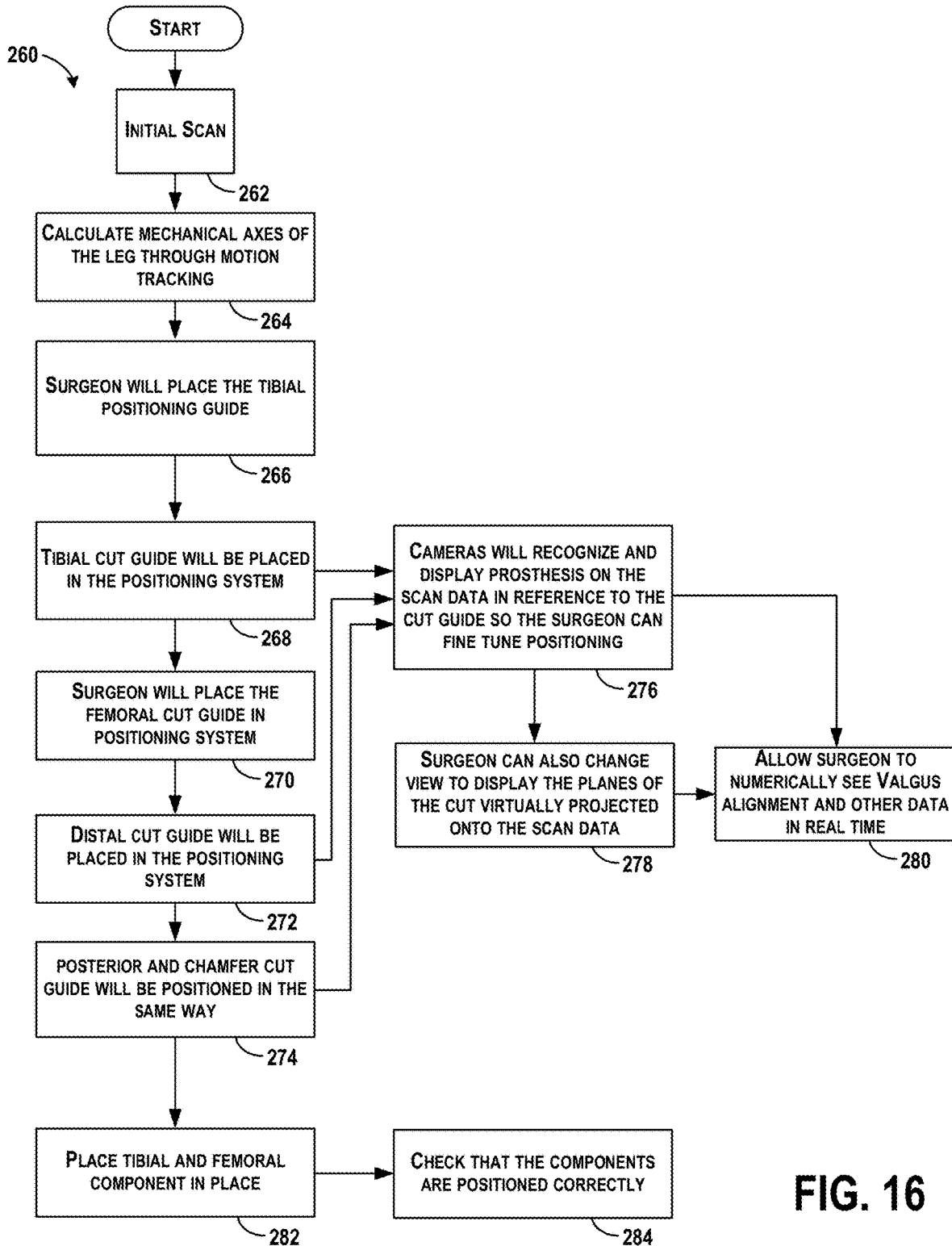
FIG. 16 shows a flowchart of another example method for positioning of a prosthesis, according to an example embodiment.

FIG. 16 shows a flowchart of another example method 260 for positioning of a prosthesis, according to an example embodiment. Initially, as shown at block 262, a scan of the bone or anatomy of the patient is performed (e.g., by the measurement device(s) 102).

As shown at block 264, the mechanical axes of the leg are calculated by the system through motion tracking. As shown at block 266, the surgeon will then place the tibial positioning guide. Following, at block 268, the tibial cut guide will be placed in the positioning system. Next, at block 270, the surgeon will place the femoral cut guide positioning system. At block 272, the surgeon will place the distal cut guide in the positioning system. At block 274, the posterior and chamfer cut guide will be positioned in the same way.

At block 276, the cameras will recognize placement of the cut guides, and the system will display the prosthesis on the scan data in reference to the cut guide positioning so that the surgeon can perform fine tune positioning. In this way, the placement of the prosthesis occurs virtually to allow the surgeon to view the placement prior to making any cuts on the patient.

At block 278, the surgeon can also change a view to display planes of the cut virtually projected onto the scan data. At block 280, the system may display numerical values, such as the valgus alignment and other data in real time.

Following, at block 282, the surgeon places the tibial and femoral components in place, and at block 284, positioning of the components is verified.

Example methods and systems thus provide live real time images with virtual guides placed to show cutting planes and/or prosthesis positions in real time, prior to making any cuts. In the operating room, cut guides can be positioned on the bone in real time, and simultaneously, the system can display cut planes and prosthesis positions virtually to visualize the reconstruction in real time. This provides a demonstration to the surgeon of where the prosthesis is to be positioned. The bone and surgical instruments have reference points that are tracked by the measurement device and/or cameras to provide a real time up-to-date image and virtual image of the cut guides positioning, as well as prosthesis alignment.

The description of the different advantageous arrangements has been presented for purposes of illustration and description, and is not intended to be exhaustive or limited to the embodiments in the form disclosed. Many modifications and variations will be apparent to those of ordinary skill in the art. Further, different advantageous embodiments may describe different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A system comprising:
   a measurement device to (i) collect information of a surface of a bone of a limb of a patient including capturing a live image of the bone, to track one or more reference points positioned on one or more bones or an anatomy of the patient, and to (ii) collect information of a surgical device to track one or more reference points positioned on a surgical device;
   one or more processors; and
   data storage including instructions executable by the one or more processors for performing functions comprising:
      tracking movement of the bone in physical space based on the tracked reference points positioned on the one or more of the bone or the anatomy of the patient;
      calculating an axis of the limb based on the tracked reference points positioned on the one or more of the bone or the anatomy of the patient;
      tracking movement of the surgical device in physical space based on the tracked reference points positioned on the surgical device; and
      providing for display a virtual image overlaid onto the live image of the bone, wherein the virtual image includes information for assisting in placement of the surgical device at a position on the bone, wherein the virtual image is overlaid at a position onto the live image of the bone based on the movement of the surgical device in physical space and includes a display of the axis of the limb.

2. The system of claim 1, wherein the function of calculating the axis of the limb comprises:
   determining the axis of the limb based on reference points positioned on a medial malleoli of the patient, a lateral malleoli of the patient, and a base of an anterior cruciate ligament of the patient.

3. The system of claim 1, wherein the function of calculating the axis of the limb comprises:
   extrapolating a point of rotation of a hip of the patient during movement of the limb based on the tracked reference points.

4. The system of claim 1, wherein the function of calculating the axis of the limb comprises:
   tracking a reference point on a distal portion of a femur of the patient;

determining a center of rotation as a point about which the distal portion of the femur rotates based on the tracked reference point on the distal portion of the femur; and determining the axis of the limb based on the center of rotation.

5. The system of claim 1, wherein the function of calculating the axis of the limb comprises:

tracking reference points on an ankle of the patient;

determining peaks of sides of the ankle based on the tracked reference points on the ankle;

determining a median point between the peaks of the sides of the ankle; and determining the axis of the limb based on a virtual line from the median point up to a point at a base of an anterior cruciate ligament of the patient.

6. The system of claim 1, wherein the function of tracking movement of the bone in physical space comprises continuously taking measurements during surgery to identify the movement of the bone.

7. The system of claim 1, wherein the function of tracking movement of the bone in physical space comprises:

tracking the one or more reference points positioned on one or more of a distal anterior tibial crest of the patient, a medial malleoli of the patient, a lateral malleoli of the patient, a reference off a medial third or other portion of the tibial tubercle of the patient, a base of an anterior cruciate ligament of the patient, and a posterior cruciate ligament and intercondylar eminences of the patient.

8. The system of claim 1, wherein the one or more processors perform the functions intraoperatively during surgery.

9. The system of claim 1, wherein the function of providing for display the virtual image further comprises:

providing for display a graphic illustrating placement of a prosthesis in relation to the bone.

10. The system of claim 1, wherein the function of providing for display the virtual image further comprises:

providing for display information indicating one or more of a lateral gap of a knee of the patient, a medial gap of the knee of the patient, an alignment of the knee of the patient, a flexion of a femoral cut, and a slope of a tibial cut.

11. The system of claim 1, wherein the function of providing for display the virtual image comprises:

displaying the virtual image including placement of the surgical device, a graphic illustrating placement of a prosthesis in relation to the bone, and information indicating one or more of a lateral gap, a medial gap, and an alignment of a knee of the patient with placement of the prosthesis.

12. The system of claim 1, further comprising:

wherein the measurement device is one or more cameras for capturing live images.

13. A method comprising:

receiving information, collected by a measurement device, of (i) a surface of a bone of a limb of a patient including capturing a live image of the bone to track one or more reference points positioned on one or more bones or an anatomy of the patient, and of (ii) a surgical device to track one or more reference points positioned on a surgical device;

tracking movement of the bone in physical space based on the tracked reference points positioned on the one or more of the bone or the anatomy of the patient;

calculating an axis of the limb based on the tracked reference points positioned on the one or more of the bone or the anatomy of the patient;

tracking movement of the surgical device in physical space based on the tracked reference points positioned on the surgical device; and providing for display a virtual image overlaid onto the live image of the bone, wherein the virtual image includes information for assisting in placement of the surgical device at a position on the bone, wherein the virtual image is overlaid at a position onto the live image of the bone based on the movement of the surgical device in physical space and includes a display of the axis of the limb.

14. The method of claim 13, further comprising:

receiving the information of the surface of the bone as exposed from the limb of the patient in real time during surgery.

15. The method of claim 13, wherein receiving the information, collected by the measurement device, of the surface of the bone of the limb of the patient comprises:

receiving the information using a scanning tool in real time during surgery.

16. The method of claim 13, further comprising:

providing a virtual view of a resection on the bone.

17. The method of claim 13, further comprising:

displaying the virtual image including placement of the surgical device, a graphic illustrating placement of a prosthesis in relation to the bone, and information indicating one or more of a lateral gap, a medial gap, and an alignment of a knee of the patient with placement of the prosthesis.

18. A non-transitory computer-readable medium having stored thereon instructions that when executed by a computing device that includes one or more processors causes the computing device to perform functions comprising:

receiving information, collected by a measurement device, of (i) a surface of a bone of a limb of a patient including capturing a live image of the bone to track one or more reference points positioned on one or more bones or an anatomy of the patient, and of (ii) a surgical device to track one or more reference points positioned on a surgical device;

tracking movement of the bone in physical space based on the tracked reference points positioned on the one or more of the bone or the anatomy of the patient;

calculating an axis of the limb based on the tracked reference points positioned on the one or more of the bone or the anatomy of the patient;

tracking movement of the surgical device in physical space based on the tracked reference points positioned on the surgical device; and providing for display a virtual image overlaid onto the live image of the bone, wherein the virtual image includes information for assisting in placement of the surgical device at a position on the bone, wherein the virtual image is overlaid at a position onto the live image of the bone based on the movement of the surgical device in physical space and includes a display of the axis of the limb.

19. The non-transitory computer-readable medium of claim 18, wherein the function of providing for display the virtual image comprises:

receiving the live image of the bone;

providing for display the live image of the bone; and displaying a virtual cutting plane onto the live image of the bone.

20. The non-transitory computer-readable medium of claim 18, wherein the function of providing for display the virtual image comprises:
   receiving the information of the bone as exposed from the limb of the patient in real time during surgery.

* * * * *